US009307999B2

(12) United States Patent
Li et al.

(10) Patent No.: US 9,307,999 B2
(45) Date of Patent: Apr. 12, 2016

(54) INTERVENTIONAL MEDICAL DEVICE CONNECTOR AND METHOD FOR USING SAME

(75) Inventors: Anning Li, Shenzhen (CN); Yilong Chen, Shenzhen (CN); Delong Zhang, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 410 days.

(21) Appl. No.: 13/818,747

(22) PCT Filed: Aug. 20, 2011

(86) PCT No.: PCT/CN2011/078677
§ 371 (c)(1),
(2), (4) Date: Feb. 25, 2013

(87) PCT Pub. No.: WO2012/025032
PCT Pub. Date: Mar. 1, 2012

(65) Prior Publication Data
US 2013/0150879 A1    Jun. 13, 2013

(30) Foreign Application Priority Data
Aug. 26, 2010   (CN) .......................... 2010 1 0265431

(51) Int. Cl.
*A61B 17/12*      (2006.01)
*A61B 17/00*      (2006.01)
*A61F 2/01*       (2006.01)

(52) U.S. Cl.
CPC ....... *A61B 17/12122* (2013.01); *A61B 17/0057* (2013.01); *A61B 17/12109* (2013.01); *A61B 2017/00477* (2013.01); *A61B 2017/00623* (2013.01); *A61B 2017/12054* (2013.01); *A61F 2/013* (2013.01); *A61F 2220/0033* (2013.01)

(58) Field of Classification Search
CPC ............... A61B 17/0057; A61B 17/12; A61B 17/12022; A61B 17/32056; A61B 2017/00358; A61B 2017/00575; A61B 2017/00623; A61B 2017/1205; A61B 2017/12054; A61F 2220/0025; A61F 2220/0033; A61F 2220/0075
See application file for complete search history.

(56) References Cited

U.S. PATENT DOCUMENTS

| | | | |
|---|---|---|---|
| 2004/0176797 A1* | 9/2004 | Opolski ........................ | 606/213 |
| 2006/0116714 A1* | 6/2006 | Sepetka et al. ................ | 606/200 |
| 2008/0300616 A1* | 12/2008 | Que et al. ..................... | 606/191 |
| 2009/0254165 A1* | 10/2009 | Tabor et al. ................... | 623/1.11 |
| 2009/0319037 A1* | 12/2009 | Rowe et al. ................... | 623/2.11 |

* cited by examiner

*Primary Examiner* — Jonathan W Miles
*Assistant Examiner* — Todd J Scherbel
(74) *Attorney, Agent, or Firm* — Raymond Sun

(57) ABSTRACT

An interventional medical device connector and a method for using same. The interventional medical device connector comprises an implant (1) and a pusher (5). One end of the implant (1) is provided with at least one lock ring (9). The top end of the pusher (5) is provided with at least one locking hole (7). The pusher (5) is provided with at least one control wire (4). The control wire (4) slides along the axial direction of the pusher (5), and the top end of the control wire (4) can reach at least one of the locking holes (7). The control wire (4), the lock ring (9) and the locking hole (7) together form a connection means having a lock-pin structure. Use of this means of connection effectively overcomes the defects of existing threaded connections, reduces risks, and provides convenience of use.

19 Claims, 14 Drawing Sheets

INTERVENTIONAL MEDICAL DEVICE CONNECTOR AND METHOD FOR USING SAME

TECHNICAL FIELD

The present invention relates to a medical device that is placed in a selected part of the human body using the catheter intervention method. In particular, the present invention relates to an interventional medical device connector and the use method thereof.

BACKGROUND

The treatment method that uses the percutaneous intervention technology to treat diseases is being used in more and more application fields. The catheter intervention treatment method can be used to place various kinds of materials, devices, and medicines in the heart, arteries and veins of the human body. For example, atrial septal defect (ASD) occluder, ventricular septal defect (VSD) occluder, patent ductus arteriosus (PDA) occluder, and patent foramen ovale (PFO) occluder, and the like can all be placed in the defective part of the heart via catheter to treat congenital heart disease.

When these devices are placed in the heart, arteries and veins of the human body using the catheter intervention method, since the heart, arteries, and veins of the human body have complicated anatomical structures, it is necessary to use a catheter, guide wire, and pusher in order to guarantee that the devices arrive at the predetermined parts. The catheter first arrives at the predetermined part under the guidance of the guide wire. When conducting this kind of surgery, it is necessary to use a very small and flexible catheter. Meanwhile, the catheter and the guide wire should be designed to have very good development under X-ray. When the catheter reaches the predetermined part, the guide wire is removed, and the device is included in the catheter and is pushed by a pusher to the end of the catheter via the channel established by the catheter. When the device reaches the end of the catheter, the device is released from the catheter. Finally, the device is broken off from the pusher.

The method that is normally used is to adopt threaded connection between the device and the pusher. After the pusher sends the device to the predetermined part, the thread is disengaged to break off the connection between the device and the pusher. This type of threaded connection can realize reliable connection between the device and the pusher and can realize controlled release at the same time. If the size of the device is selected inappropriately or the device is poorly expanded, the device can be included into the transportation catheter again, placed again, and finally released reliably. Under some circumstances, the device can also be removed from the human body via the catheter and replaced with a new appropriate device to be placed again.

This type of threaded connection method has a lot of limitations. The threaded connection is a hard connection. The degree of freedom of the device in the radial direction will be hindered before the device is released. As a result, the device is unable to adapt well to the anatomical structure of the predetermined part, and the doctor is unable to evaluate well the effect after the device is implanted (such as the occluding effect of an occluder). When a threaded connection is adopted, it is necessary to form threads on the device to be implanted. It is usually necessary to use a certain amount of metal material to form this part. As a result, the amount of the metal implanted into the human body is increased. The metal material used for the threaded connection part is usually different from the metal material used for the main body of the device. As a result, electrochemical corrosion occurs over the long term between the different metal parts of the implanted device, which shortens the safe service life of the device and increases the patient's long-term risk. The threaded connection needs a sufficient number of spirals in order to guarantee reliability. Therefore, it is necessary to rotate the pusher many rounds in order to disengage the connection. This requires a relatively long time during the operation conducted by the doctor. As a result, the surgical risk is increased.

DISCLOSURE OF THE INVENTION

The objective of the present invention is to provide an interventional medical device connector and the use method thereof that can solve the problems of the existing threaded connection method.

The technical scheme of the present invention is as follows:

An interventional medical device connector including an implant and a pusher, wherein at least one locking ring is provided at one end of said implant; at least one locking hole is provided at the top end of said pusher; said pusher is provided with at least one control wire; said control wire slides along the axial direction of the pusher; the top end of the control wire can reach at least one of said locking holes; said control wire, locking ring, and locking hole together form a connection means having a lock-pin structure.

Said interventional medical device connector, wherein a lock is provided at the top end of said pusher, and all of said locking rings are provided on said lock.

Said interventional medical device connector, wherein said lock has a cylindrical shape; its top end is sealed; and outer surface of the top end is recessed and forms a conjugate spherical surface with the surface at the end of said implant.

Said interventional medical device connector, wherein there is one said locking ring and there is one said locking hole.

Said interventional medical device connector, wherein there are two said locking rings provided symmetrically on the two sides of the end of the implant, and there are two said locking holes provided symmetrically on the two sides of the top end of said pusher.

Said interventional medical device connector, wherein there are two said locking rings provided symmetrically on the two sides of the end of the implant, and there are four said locking holes provided symmetrically on the two sides of the top end of said pusher and disposed along the axial direction of the pusher.

Said interventional medical device connector, wherein said locking hole has a slot shape, round shape, or oval shape.

Said interventional medical device connector, wherein said locking ring is formed by weaving a plurality of metal wires.

Said interventional medical device connector, wherein said locking ring is kept in the state of nestling up against the surface of the implant when the implant and the pusher are in the disengaged state.

Said interventional medical device connector, wherein said implant and locking ring are made of the same material.

Said interventional medical device connector, wherein a cavity is provided in said pusher and is connected to said locking hole, and said control wire is placed in the cavity of said pusher.

Said interventional medical device connector, wherein said pusher is a spring tube densely wound with metal wires.

A use method of interventional medical device connector having the following steps:

inserting a catheter into the human body such that the far end of said catheter reaches a predetermined part in the body; keeping said interventional medical device connector in a locked state; including said interventional medical device connector in said catheter; sending said implant to said predetermined part via said catheter; pulling back the control wire on said pusher; removing the catheter and the pusher.

The present invention has the following beneficial effects. The interventional medical device connector of the present invention adopts an implant having one or a plurality of locking rings and a pusher having a locking hole and control wire. The medical device is locked and unlocked through the lock-pin connection function of the locking ring, locking hole, and control wire. The locking ring on the implant is locked with the locking hole on the pusher so that they can be connected to each other stably. One or a plurality of control wires penetrates the locking ring of the implant to form a lock-pin structure so that the implant and the pusher are locked. When the control wire retracts along the axial direction of the pusher, the implant and the pusher are unlocked. The connector of the present invention can be used to effectively solve the problems of the existing threaded connection means.

BRIEF DESCRIPTION OF THE DRAWINGS

FIG. 1A-2 is a partially enlarged view of FIG. 1A-1.
FIG. 1A-3 is a cross-sectional view of FIG. 1A-2.
FIG. 1B-1 is a diagram illustrating the process of unlocking the interventional medical device connector disclosed in the first embodiment of the present invention.
FIG. 1B-2 is a partially enlarged view of FIG. 1B-1.
FIG. 1B-3 is a cross-sectional view of FIG. 1B-2.
FIG. 1C-1 is a diagram illustrating the state when unlocking the interventional medical device connector disclosed in the first embodiment of the present invention is completed.
FIG. 1C-2 is a partially enlarged view of FIG. 1C-1.
FIG. 1C-3 is a cross-sectional view of FIG. 1C-2.
FIG. 2A-1 is a diagram illustrating the locked state of the interventional medical device connector disclosed in the second embodiment of the present invention.
FIG. 2A-2 is a partially enlarged view of FIG. 2A-1.
FIG. 2A-3 is a cross-sectional view of FIG. 2A-2.
FIG. 2B-1 is a diagram illustrating the process of unlocking the interventional medical device connector disclosed in the second embodiment of the present invention.
FIG. 2B-2 is a partially enlarged view of FIG. 2B-1.
FIG. 2B-3 is a cross-sectional view of FIG. 2B-2.
FIG. 2C-1 is a diagram illustrating the state when unlocking the interventional medical device connector disclosed in the first embodiment of the present invention is completed.
FIG. 2C-2 is a partially enlarged view of FIG. 2C-1.
FIG. 2C-3 is a cross-sectional view of FIG. 2C-2.
FIG. 3A-1 is a diagram illustrating the locked state of the interventional medical device connector disclosed in the third embodiment of the present invention.
FIG. 3A-2 is a partially enlarged view of FIG. 3A-1.
FIG. 3A-3 is a cross-sectional view of FIG. 3A-2.
FIG. 3B-1 is a diagram illustrating the process of unlocking the interventional medical device connector disclosed in the first embodiment of the present invention.
FIG. 3B-2 is a partially enlarged view of FIG. 3B-1.
FIG. 3B-3 is a cross-sectional view of FIG. 3B-2.
FIG. 3C-1 is a diagram illustrating the state when unlocking the interventional medical device connector disclosed in the third embodiment of the present invention is completed.
FIG. 3C-2 is a partially enlarged view of FIG. 3C-1.
FIG. 3C-3 is a cross-sectional view of FIG. 3C-2.

DETAILED DESCRIPTION

Figures 1, 1A:
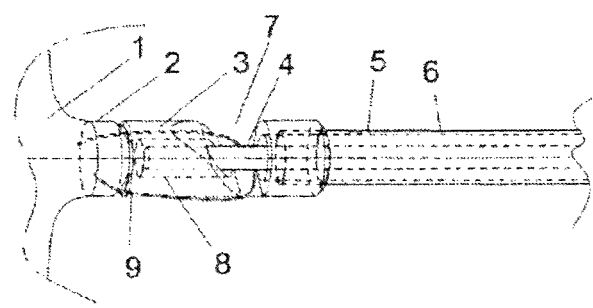
FIG. 1A-1 is a diagram illustrating the locked state of the interventional medical device connector disclosed in the first embodiment of the present invention.
Figures 1, 1A, 2:
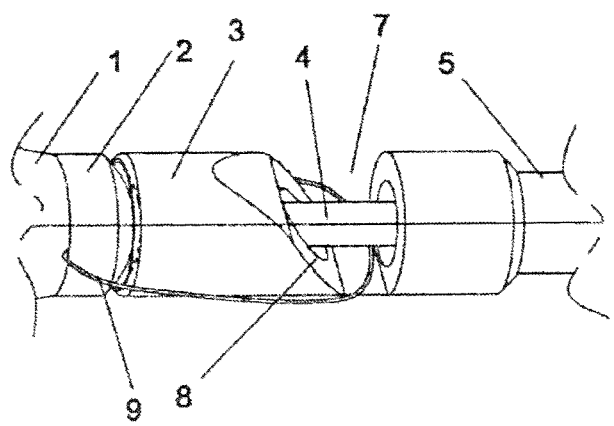

The interventional medical device connector of the present invention adopts an implant having one or a plurality of locking rings and a pusher having a locking hole and control wire. The medical device is locked and unlocked through the lock-pin connection function of the locking ring, locking hole, and control wire. The locking ring on the implant is locked with the locking hole on the pusher so that they can be connected to each other stably. One or a plurality of control wires penetrates the locking ring of the implant to form a lock-pin structure so that the implant and the pusher are locked. When the control wire retracts along the axial direction of the pusher, the implant and the pusher are unlocked.

In order to further clarify the objective, technical scheme, and merits of the present invention, the present invention will be explained in more detail below based on embodiments with reference to the attached figures.

Embodiment 1

As shown in FIGS. 1A-1-1A-3, the interventional medical device connector disclosed in the first embodiment of the present invention includes implant 1 and pusher 5.

Said implant 1 can be a cardiac occluder or a vascular plug for arteries or veins. It can also be a thrombus filter or other implant with a tail end. The structures of these devices are well known to those skilled in this field and will not be described in details.

The normal cardiac occluder or vascular plug is formed by weaving nickel-titanium alloy wires and has a closure head 2 at one end. In order to realize the objective of this embodiment, a locking ring 9 is welded to said closure head 2. As shown in FIG. 1A-2 and FIG. 1C-2, the locking ring 9 has a loop portion and two separate ends that are secured to the closure head 2. The loop portion of the locking ring 9 is positioned adjacent to a surface of the implant 1 when the locking ring 9 is dis-engaged from the lock of the pusher 5. This positioning of the locking ring 9 against the surface of the implant 1 shall be referred to herein as "nestling up". The top of closure head 2 is polished to a spherical surface. Locking ring 9 can be formed by weaving a plurality of nickel-titanium alloy wires. It can be provided with better flexibility through a high-temperature heat treatment. Also, locking ring 9 can be kept in a state of nestling up against the surface of implant 1 to prevent locking ring 9 from sticking out and to facilitate climb-over of the endothelial tissue to lower the risk for thrombus. Implant 1, closure head 2, and locking ring 9 can be made of the same material to prevent electrochemical corrosion between different kinds of metals in the blood environment to improve the safety degree of implant 1.

Pusher 5 can use a spring tube densely wound with metal wires. Lock 3 having a cavity 8 and a locking hole 7 is welded to the top end of pusher 5. Pusher 5 is coaxial with locking 3. The cavity 8 of locking 3 is connected to the tube cavity 6 of pusher 5. A control wire 4 is installed in tube cavity 6 of pusher 5. Control wire 4 can move along the axial direction in tube cavity 6 and cavity 8. The top end of control wire 4 can reach locking hole 7. Lock 3 has an approximately cylindrical shape, and its head is sealed. A recessed spherical groove is formed at the top of lock 3. This groove can just accommodate closure head 2 and allow it to rotate in close contact. In this embodiment, locking hole 7 has a slot shape, which is formed by scooping out part of the sidewall in the middle part of lock 3. The locking hole can also be formed in a round shape or oval shape.

The surface of closure head 2 and the surface at the top end of lock 3 are conjugate spherical surfaces. Closure head 2 can fit and rotate in the top end of lock 3.

To make connection, closure head 2 is moved toward lock 3 while facing the lock. Locking ring 9 is inserted into locking hole 7. Then, control wire 4 is let to slide along the axial direction toward implant 1 until the top end of control wire 4 is close to the cavity 8 of lock 3. Then, the top end of control wire 4 penetrates locking hole 9 to connect implant 1 with pusher 5. After that, control wire 4 further slides until it is abutted against the top of the cavity 8 of lock 3 to realize locking between implant 1 and pusher 5.

As shown in FIGS. 1B-1-1B-3, control wire 4 is let to slide along the axial direction of the tube cavity of pusher 5 toward the far end of pusher 5, that is, move in the opposite direction. The top end of control wire 4 first separates from the top part of cavity 8 of lock 3. When the top end of control wire 4 returns to the tube cavity 6 of pusher 5, control wire 4 is separated from locking ring 9, and locking ring 9 pops out from locking hole 7 depending on the elasticity.

As shown in FIGS. 1C-1-1C-3, because of the super elasticity of the nickel-titanium alloy, without the support of an external force, locking ring 9 will quickly resume the original shape to nestle up against the surface of implant 1. Then, pusher 5 is removed to separate implant 1 from pusher 5 to complete release of implant 1 in the human body.

In fact, both implant 1 and pusher 5 will be included in a catheter during an intervention surgery. A certain space can be kept between the inner wall of the catheter and the outer wall of pusher 5. Control wire 4 can be disposed in that space so that it can slide nearly parallel with pusher 5. Since control wire 4 is basically outside pusher 5, it is only necessary to form the cavity at the top end of pusher 5 but not in the rest of the pusher. When making connection, locking ring 9 is first inserted into locking hole 7. Then, the top end of control wire 4 is slightly bent to penetrate locking hole 7 and be inserted into the cavity at the top end of pusher 5. Meanwhile, control wire 4 also penetrates locking ring 9 until the top end of control wire 4 reaches the top part of cavity 8 to complete the connection between implant 1 and pusher 5. During the transportation process of the catheter, pusher 5 causes control wire 4 to move along with it in the catheter while the connector is kept in the locked state. Control wire 4 is let to slide in the opposite direction to separate from locking hole 7 and locking ring 9. Locking ring 9 pops out from locking hole 7 to disconnect implant 1 from pusher 5.

The structure of the pusher in this embodiment can be slightly simplified without using the single lock. More specifically, the metal wires at the top end of the spring tube pusher are welded tight to form a section of solid tube wall, and the locking hole is directly formed on that tube wall. The metal wires at the top end of the pusher can be formed into a disc and welded into a sealed end. Then, it is polished to a smooth state. It is equivalent to the top end of the lock.

Embodiment 2

As shown in FIGS. 2A-1-2A-3, the structure of the interventional medical device connector disclosed in the second embodiment of the present invention is basically the same as that of the interventional medical device connector disclosed in the first embodiment. The difference is that a first locking ring 91 and a second locking ring 92 are welded on closure head 2 at the sealed end of implant 1. Both of the first locking ring 91 and the second locking ring 92 are formed by weaving nickel-titanium alloy wires and are provided symmetrically on the two sides of the closure head 2. These two locking rings can provide a balanced pulling force on the two sides to keep implant 1 on the same axial line as pusher 5 during the connection. Implant 1 will not deviate to one side. Two locking holes, that is, the first locking hole 71 and the second locking hole 72 are formed on lock 3. The first locking hole 71 and the second locking hole 72 are formed symmetrically on the two sides of lock 3. The first locking hole 71 and the second locking hole 72 have a round shape or oval shape. That is, the locking holes are formed by symmetrically scooping out two parts of the sidewall in the middle part of lock 3.

To make connection, closure head 2 is moved toward lock 3 while facing the lock. The first locking ring 91 is inserted into the first locking hole 71 such that it can stick out from the second locking hole 72. The second locking ring 92 is inserted into the second locking hole 72 such that it can stick out from the first locking hole 71. In other words, the first locking ring 91 and the second locking ring 92 are superimposed with each other in the lock. Then, control wire 4 is let to slide along the axial direction toward implant 1 until the top end of control wire 4 is close to the cavity 8 of lock 3. Then, the top end of control wire 4 penetrates the first locking ring 91 and the second locking ring 92 (penetrate the two locking rings at the same time). After that, control wire 4 is let to further slide until it is abutted against the top part of cavity 8 of lock 3 to realize locking between implant 1 and pusher 5.

As shown in FIGS. 2B-1-2B-3, control wire 4 is let to slide along the axial line of the tube cavity of pusher 5 in the opposite direction. The top end of control wire 4 is separated from the first locking ring 91 and the second locking ring 92 (separated from the two rings at the same time) until the top end of control wire 4 returns into the tube cavity 6 of pusher 5. At that time, the first locking ring 91 and the second locking ring 92 will pop out from the first locking hole 71 and the second locking hole 72, respectively. The first locking ring 91 and the second locking ring 92 resumes the original shape and nestle up against the surface of implant 1.

As shown in FIGS. 2C-1-2C-3, when pusher 5 is removed, implant 1 is separated from pusher 5. Implant 1 is released from pusher 5.

Embodiment 3

Figures 1, 1A, 2, 3:
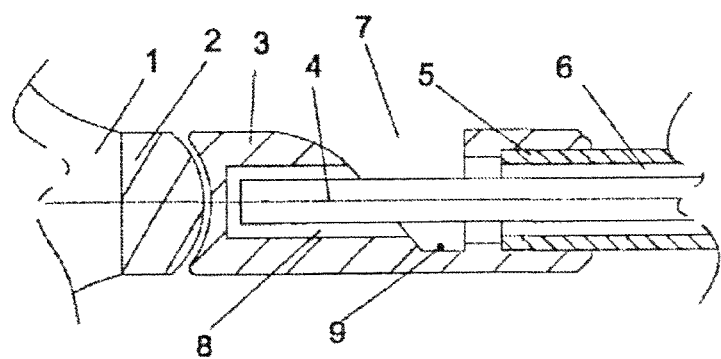
Figures 1, 1B:
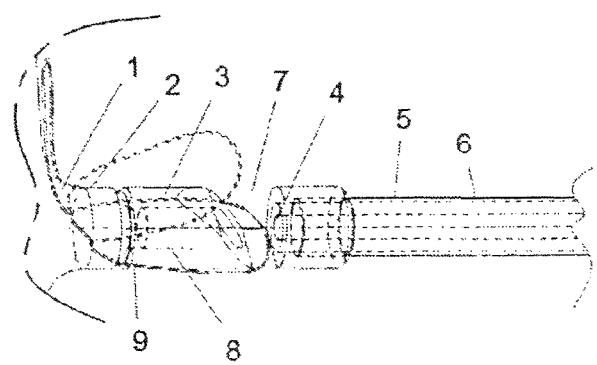
Figures 1, 1B, 2:
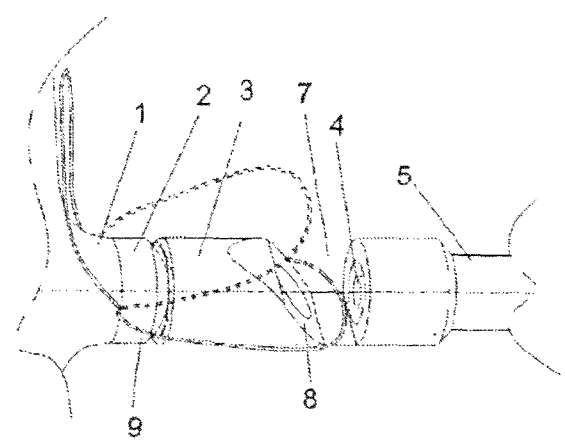
Figures 1, 1B, 2, 3:
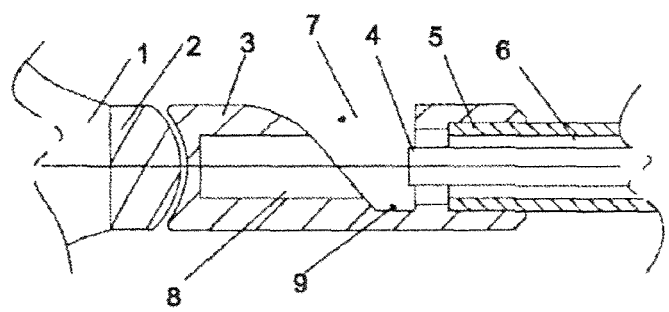
Figures 1, 1C:
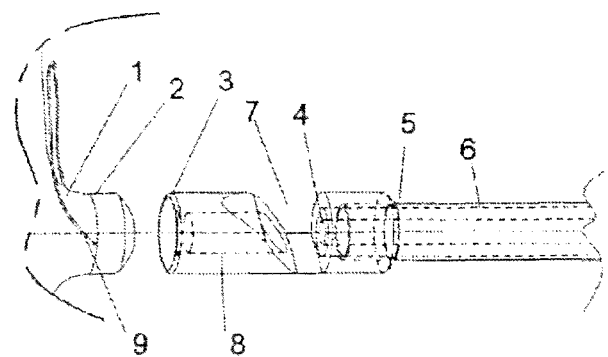
Figures 1, 1C, 2:
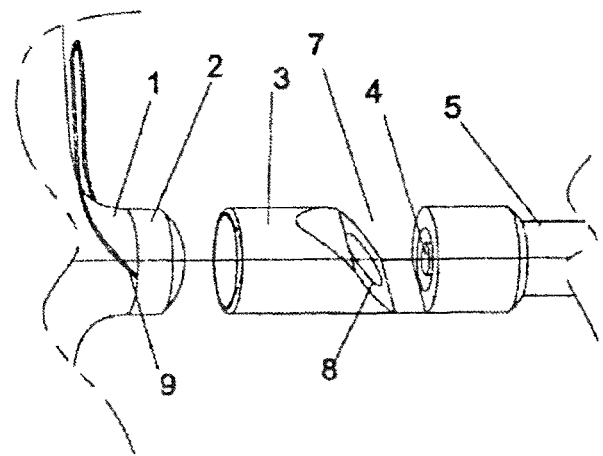
Figures 1, 1C, 2, 3:
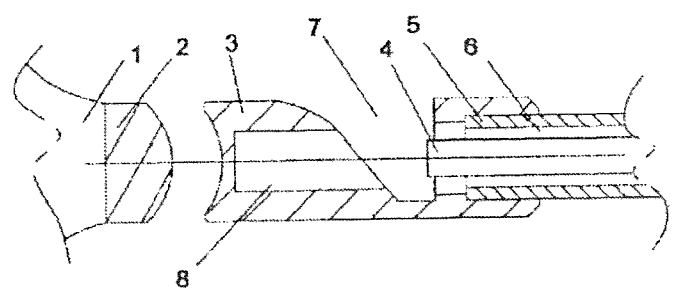
Figures 1, 2A:
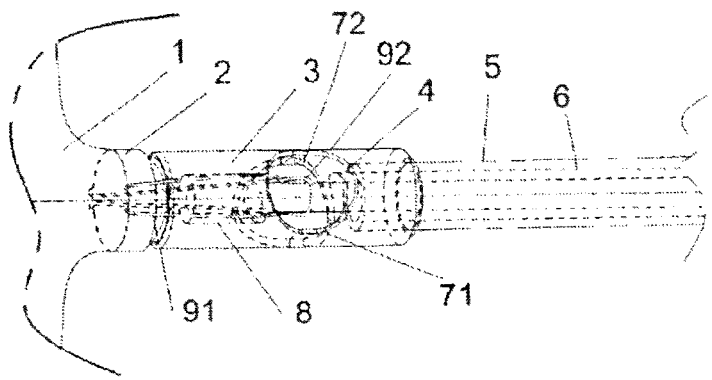
Figures 2, 2A:
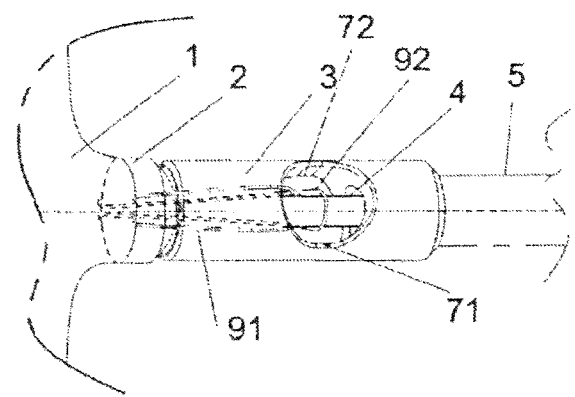
Figures 2, 2A, 3:
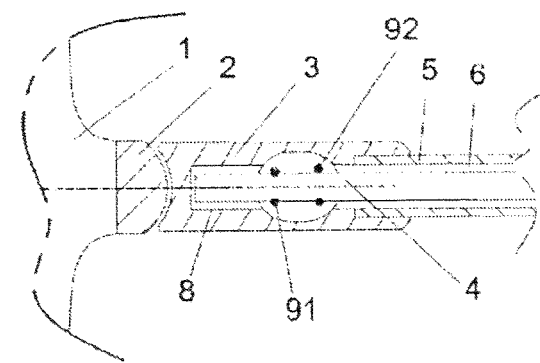
Figures 1, 2B:
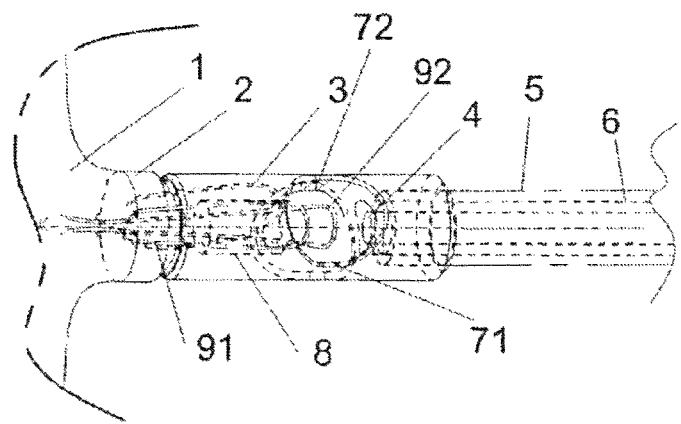
Figures 2, 2B:
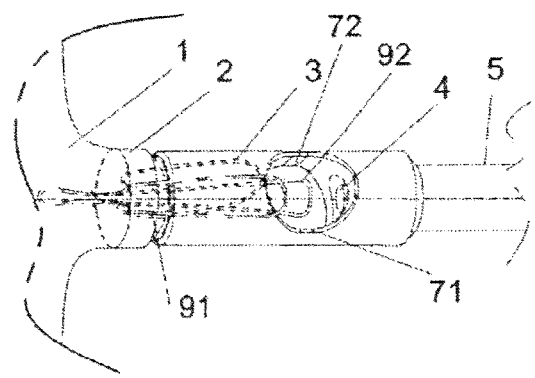
Figures 2, 2B, 3:
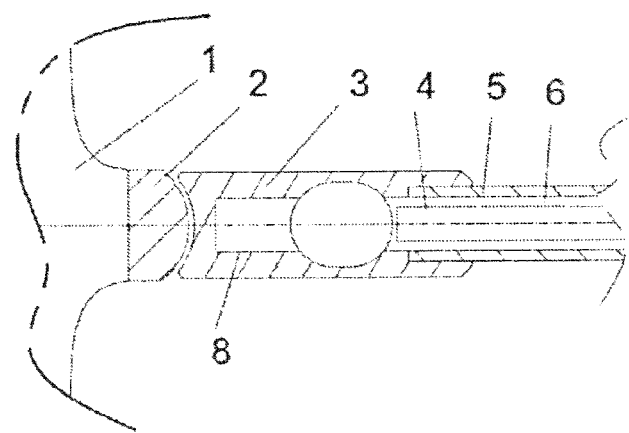
Figures 1, 2C:
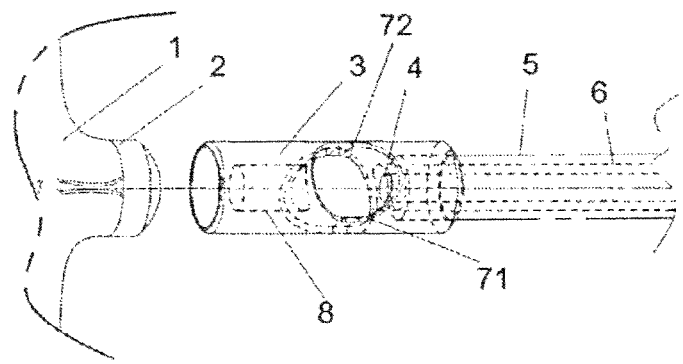
Figures 2, 2C:
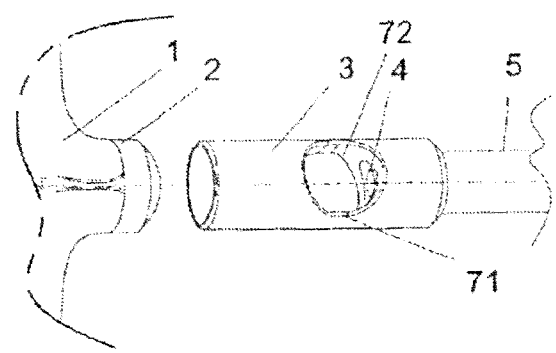
Figures 2, 2C, 3:
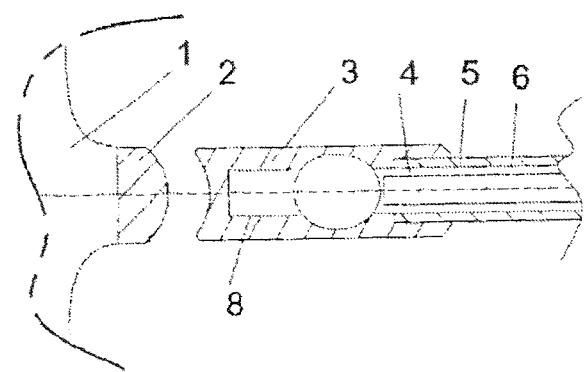
Figures 1, 3A:
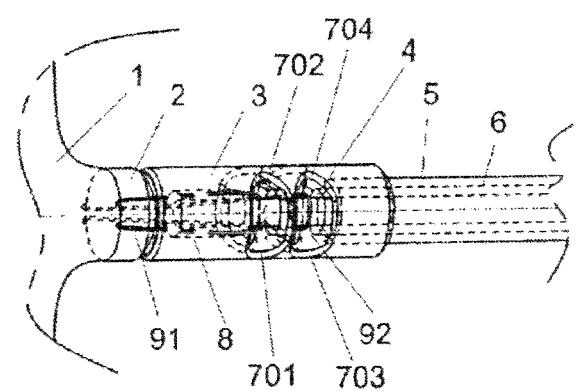
Figures 2, 3A:
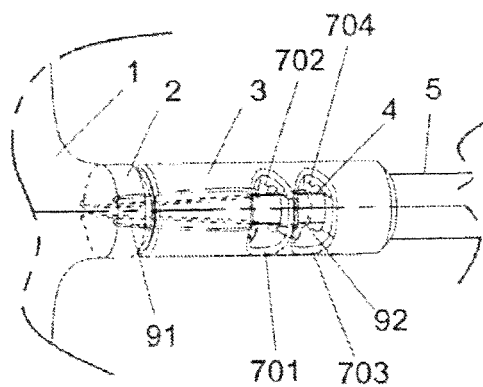
Figures 3, 3A:
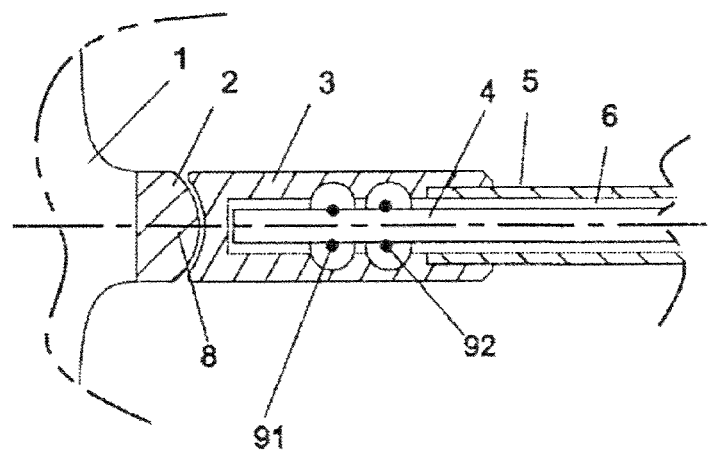

As shown in FIGS. 3A-1-3A-3, the structure of the interventional medical device connector disclosed in the third embodiment of the present invention is basically the same as that of the interventional medical device connector disclosed in the second embodiment. The difference is that four locking holes, that is, the first locking hole 701, the second locking hole 702, the third locking hole 703, and the fourth locking hole 704 are provided on the lock in order to facilitate insertion of the locking rings into the locking holes. The four locking holes have a round or oval shape. The first locking hole 701 and the second locking hole 702 are provided symmetrically on the two sides of lock 3. The third locking hole 703 and the fourth locking hole 704 are provided symmetrically on the two sides of lock 3. The first locking hole 701 and the third locking hole 703 are arranged along the axial direction of lock 3. The second locking hole 702 and the fourth locking hole 704 are arranged along the axial direction of lock 3.

To make connection, closure head 2 is moved toward lock 3 while facing the lock. The first locking ring 91 is inserted into the first locking hole 701 such that it can stick out from the second locking hole 702. The second locking ring 92 is inserted into the fourth locking hole 704 such that it can stick out from the third locking hole 703. In other words, the first locking ring 91 and the second locking ring 92 are superimposed with each other in the lock. Then, control wire 4 is let to slide along the axial direction toward implant 1 until the top end of control wire 4 is close to the cavity 8 of lock 3. Then, the top end of control wire 4 penetrates the first locking ring 91 and the second locking ring 92 (penetrate the two locking rings successively). After that, control wire 4 is let to further slide until it is abutted against the top part of cavity 8 of lock 3 to realize locking between implant 1 and pusher 5.

Figures 1, 3B:
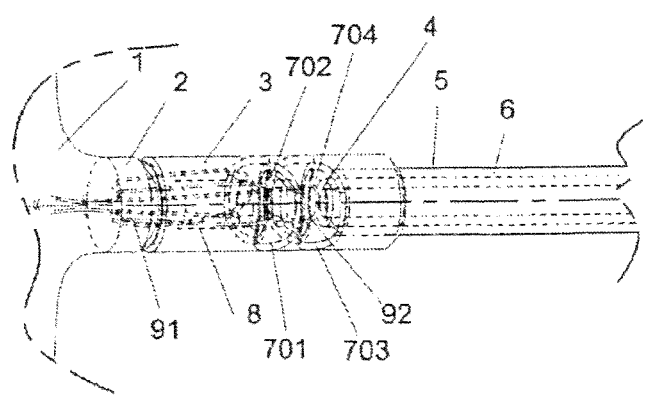
Figures 2, 3B:
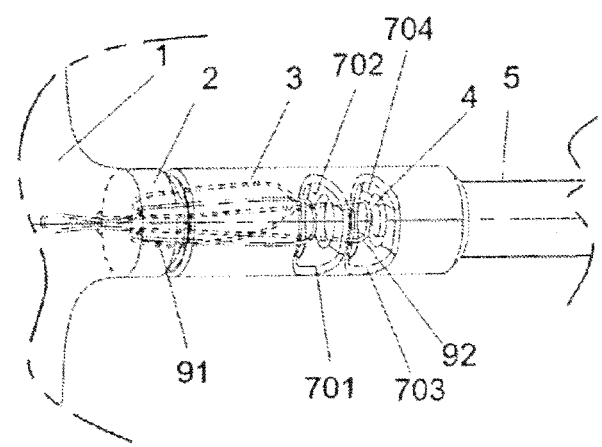
Figures 3, 3B:
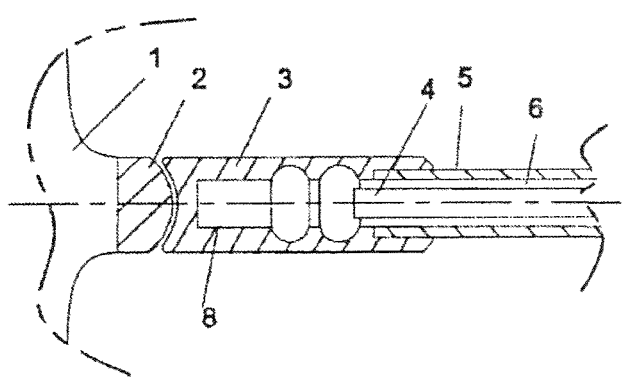

As shown in FIGS. 3B-1-3B-3, control wire 4 is let to slide along the axial line of the tube cavity of pusher 5 in the opposite direction. The top end of control wire 4 is separated from the first locking ring 91 and the second locking ring 92 (separated from the two rings successively) until the top end of control wire 4 returns into the tube cavity 6 of pusher 5. At that time, the two locking rings will pop out from the first locking hole 701 and the fourth locking hole 704, respectively. The two locking rings resume the original shape and nestle up against the surface of implant 1.

Figures 1, 3C:
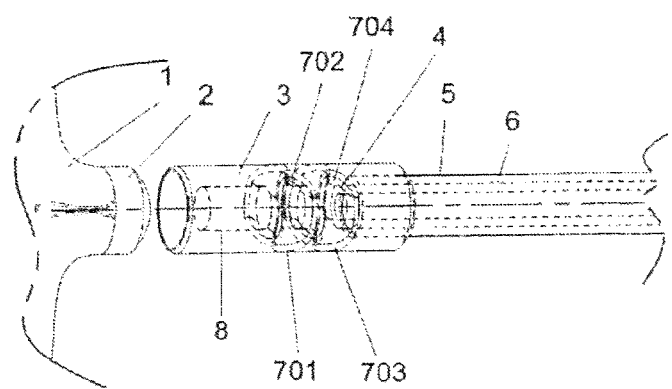
Figures 2, 3C:
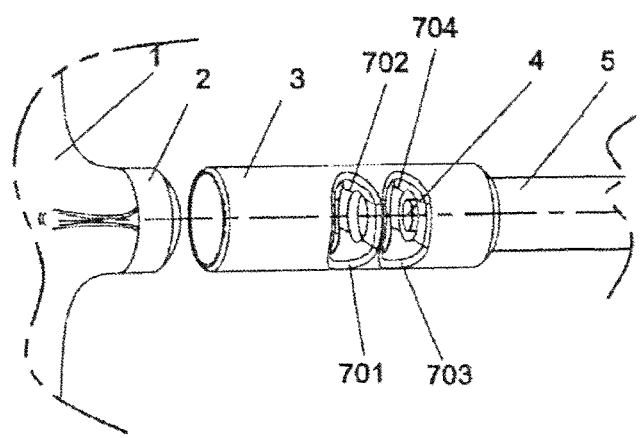
Figures 3, 3C:
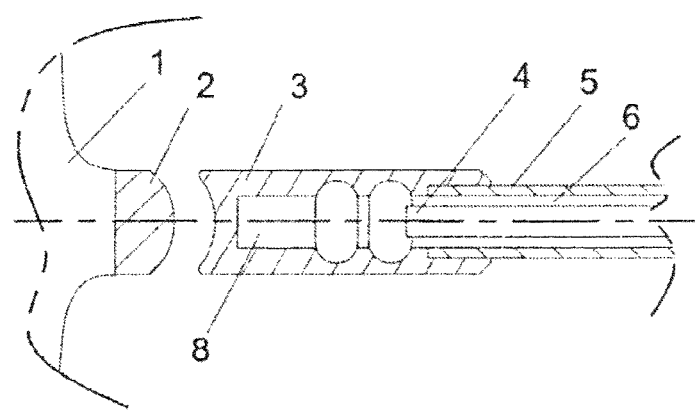

As shown in FIGS. 3C-1-3C-3, when pusher 5 is removed, implant 1 is separated from pusher 5. Implant 1 is released from pusher 5.

Embodiment 4

A common inferior vena cava thrombosis filter is manufactured by engraving a nickel-titanium alloy tube with a laser. Its end is formed into a small and short tubular shape. A locking ring formed by winding metal wires is welded to the tubular end of the filter. The locking ring can be formed by weaving a plurality of nickel-titanium alloy wires. Through a heat treatment, the locking ring can be kept in a state of nestling up against the outer surface of the tubular end to prevent the locking ring from sticking out to lower the risk for thrombus. The thrombus filter and the locking ring can be made of the same material to prevent electrochemical corrosion between different kinds of metals in the blood environment to improve the safety.

The pusher is manufactured in a similar way as described in the previous embodiments. The top end of the pusher can be flat. When making connection, the tubular end of the thrombus filter is abutted against the top end of the pusher, and the locking ring is inserted into the locking hole. The other steps are also similar to those of the previous embodiments. The thrombus filter can be separated from the pusher in the same way. The locking ring bounces back to the outer surface of the tubular end of the thrombus filter and is kept in the state of nestling up against the surface.

The present invention also provides the use method of the aforementioned interventional medical device connector. This use method has the following steps:

inserting a catheter into the human body such that the far end of said catheter reaches a predetermined part in the body;

keeping said interventional medical device connector in a locked state;

including said interventional medical device connector in said catheter;

sending said implant to said predetermined part via said catheter;

pulling back the control wire on said pusher;

removing the catheter and the pusher.

It should be understood that the present invention is not limited to the embodiments described above. Those skilled in this field can make modifications or changes based on the aforementioned explanation. All of these modifications and changes should be covered by the protection scope of the claims of the present invention.

What is claimed is:

1. A medical assembly comprising an implant and a pusher, wherein:
   the implant has a locking ring provided at an end of the implant;
   the pusher has a locking hole provided at a top end of the pusher, and a control wire that slides along an axial direction of the pusher, with the control wire having a top end which extends through the locking hole;
   the locking ring is retained inside the locking hole with the control wire extending across the locking hole when the implant is coupled to the pusher by the control wire; and
   the locking ring is made from a shape memory material such that the locking ring is biased to transition to be positioned against a surface of the implant when the locking ring is dis-engaged from the pusher.

2. The assembly of claim 1, wherein the locking ring has two ends secured to the implant at two separate locations of the implant.

3. The assembly of claim 2, wherein the implant has a lock section to which the locking ring is secured, the lock section having a concave shape, and wherein the top end of the pusher has a recessed convex shape, so that the top end of the pusher and the lock section define complementary conjugate spherical surfaces.

4. The assembly of claim 2, wherein the locking ring is a first locking ring, and the locking hole is a first locking hole, further including a second locking ring and a second locking hole, with the two locking rings provided symmetrically on two sides of the end of the implant, and where the two locking holes are provided symmetrically on two sides of the top end of the pusher.

5. The assembly of claim 2, wherein the locking ring is a first locking ring, and the locking hole is a first locking hole, further including a second locking ring, and second, third and fourth locking holes, with the two locking rings provided symmetrically on two sides of the end of the implant, and where the four locking holes are provided symmetrically on two sides of the top end of the pusher and disposed along the axial direction of the pusher.

6. The assembly of claim 2, wherein the locking hole has a slot shape, a round shape, or an oval shape.

7. The assembly of claim 2, wherein the locking ring is formed by weaving a plurality of metal wires.

8. The assembly of claim 2, wherein the implant and the locking ring are made of the same material.

9. The assembly of claim 2, wherein the pusher includes a cavity that is connected to the locking hole, with the control wire positioned in the cavity.

10. The assembly of claim 2, wherein the pusher is a spring tube densely wound with metal wires.

11. A method of using the connector of claim 1, comprising the steps of:
   coupling the implant to the pusher by locking the locking ring into the locking hole;
   inserting the catheter into a human body such that the far end of the catheter reaches a predetermined part in the body;
   delivering the implant to the predetermined part via the catheter while maintaining the locking ring in a locked state;
   withdrawing the control wire on the pusher; and
   removing the catheter and the pusher.

12. A medical assembly comprising an implant and a pusher, wherein:
   the implant has a locking ring provided at an end of the implant;
   the pusher has a locking hole provided at a top end of the pusher, and a control wire that slides along an axial direction of the pusher, with the control wire having a top end which extends through the locking hole;
   wherein the locking ring is retained inside the locking hole with the control wire extending across the locking hole when the implant is coupled to the pusher by the connector, and the locking ring is normally biased to disengage from the locking hole to transition to be positioned against a surface of the implant when the control wire does not extend across the locking hole; and
   wherein the implant has a lock section to which the locking ring is secured, the lock section having a concave shape, and wherein the top end of the pusher has a recessed convex shape, so that the top end of the pusher and the lock section define complementary conjugate spherical surfaces.

13. The assembly of claim 12, wherein the locking ring is positioned adjacent to a surface of the implant when the locking ring is dis-engaged from the pusher.

14. The assembly of claim 13, wherein the locking ring is a first locking ring, and the locking hole is a first locking hole, further including a second locking ring and a second locking hole, with the two locking rings provided symmetrically on two sides of the end of the implant, and where the two locking holes are provided symmetrically on two sides of the top end of the pusher.

15. The assembly of claim 13, wherein the locking ring is a first locking ring, and the locking hole is a first locking hole, further including a second locking ring, and second, third and fourth locking holes, with the two locking rings provided symmetrically on two sides of the end of the implant, and where the four locking holes are provided symmetrically on two sides of the top end of the pusher and disposed along the axial direction of the pusher.

16. The assembly of claim 13, wherein the locking hole has a slot shape, a round shape, or an oval shape.

17. The assembly of claim 13, wherein the locking ring is formed by weaving a plurality of metal wires.

18. The assembly of claim 13, wherein the pusher includes a cavity that is connected to the locking hole, with the control wire positioned in the cavity.

19. The assembly of claim 13, wherein the pusher is a spring tube densely wound with metal wires.

* * * * *